United States Patent [19]

Hanz et al.

[11] Patent Number: 4,625,116

[45] Date of Patent: Nov. 25, 1986

[54] STRUCTURE FOR SUPPORTING A DETECTOR HEAD

[75] Inventors: George J. Hanz, Bloomingdale, Ill.; Guenter Jung, Roettenbach; Michael Pflaum, Aisch, both of Fed. Rep. of Germany

[73] Assignee: Siemens Gammasonics, Inc., Des Plaines, Ill.

[21] Appl. No.: 717,763

[22] Filed: Mar. 29, 1985

[51] Int. Cl.$^4$ .............................................. G01T 1/20
[52] U.S. Cl. ................................................ 250/363 S
[58] Field of Search ....... 250/363 S, 363 SB, 363 SC, 250/363 SF; 378/189

[56] References Cited

U.S. PATENT DOCUMENTS

| | | | |
|---|---|---|---|
| 4,011,453 | 3/1977 | Delaby | 250/363 SF |
| 4,216,381 | 8/1980 | Lange | 250/363 SC |
| 4,417,143 | 11/1983 | Haas et al. | 250/363 SC |

Primary Examiner—Janice A. Howell
Attorney, Agent, or Firm—Mark H. Jay

[57] ABSTRACT

A structure for supporting a detector head of a radiation detector which comprises an arm having a distal end supporting the head, a base, a joint mounted on the base and moveably supporting the arm and a slotted member rotatably mounted to the base in a predetermined distance from the joint. The slotted member includes a guidance slot. It also contains a mounting mechanism for mounting the arm in the guidance slot at a desired distance from the rotational axis in a manner that the arm is freely slidable along its longitudinal arm axis, and is non-rotatably fixed with respect to the guidance slot. A motor drive rotates the slotted member about its rotational axis.

14 Claims, 8 Drawing Figures

STRUCTURE FOR SUPPORTING A DETECTOR HEAD

BACKGROUND OF THE INVENTION

1. Field of the Invention

The present invention relates to a structure for supporting a detector head of a radiation detector, such as for example the camera head of an Anger-type scintillation gamma camera.

2. Description of the Prior Art

U.S. Pat. No. 4,417,143 describes a supporting structure for driving the camera head of an emission computerized tomography (ECT) Anger-type scintillation camera. A support arm, carrying the camera head at one end and a counterweight at the other, is mounted on a universal joint and driven about the joint by a crank. The crank comprises an acme-type screw and the arm attaches to the crank at a point distant from the joint by means of an acme nut. The tilt angle of the arm is varied the position of the acme nut on the acme screw. For compensating different distances between the point of attachment of the support arm to the crank and the universal joint under different tilt angles a relatively complicated telescoping coupling member has to be utilized for the support arm.

U.S. Pat. No. 4,216,381 illustrates another supporting structure for driving the camera head of an ECT scintillation gamma camera, which comprises an upright circular frame having an outer circular ring and a concentric inner circular ring adapted for concentric relative rotation. An elongated frame of two support arms, which supports the camera head on its one end and a counterweight on its other end between the support arms, is tiltably mounted within the inner circular ring of the circular frame.

SUMMARY OF THE INVENTION

Objects

It is an object of this invention to provide for an improved structure for supporting a detector head of a radiation detector which allows for a technically simple distance compensation under different tilting angles, when a support arm for the detector head is mounted on a universal joint under different tilting angles and is driven about the joint by a crank.

Summary

According to this invention, a structure for supporting a detector head is provided which comprises (a) an arm having a distal end supporting the head and having a longitudinal arm axis;

(b) a base;

(c) a joint mounted on the base and moveably supporting the arm;

(d) a slotted member rotatably mounted to the base at a predetermined distance from the joint, said slotted member including means for mounting the arm in the guidance slot at a predetermined distance from the rotational axis in a manner that the arm is freely slidable along its longitudinal arm axis, and is non-rotatably fixed with respect to the guidance slot; and (e) means connected between base and slotted member for rotating the slotted member about its rotational axis.

Making use of a supporting structure comprising a rotatable slotted member having the above-mentioned features in a technically simple manner solves the problem of distance compensation. The supporting structure itself becomes less complicated and bulky.

The foregoing and other objects, features and advantages of the invention will be apparent from the following more particular description of a preferred embodiment of the invention, as illustrated in the accompanying drawings.

DETAILED DESCRIPTION OF THE PREFERRED EMBODIMENTS

Figure 1:
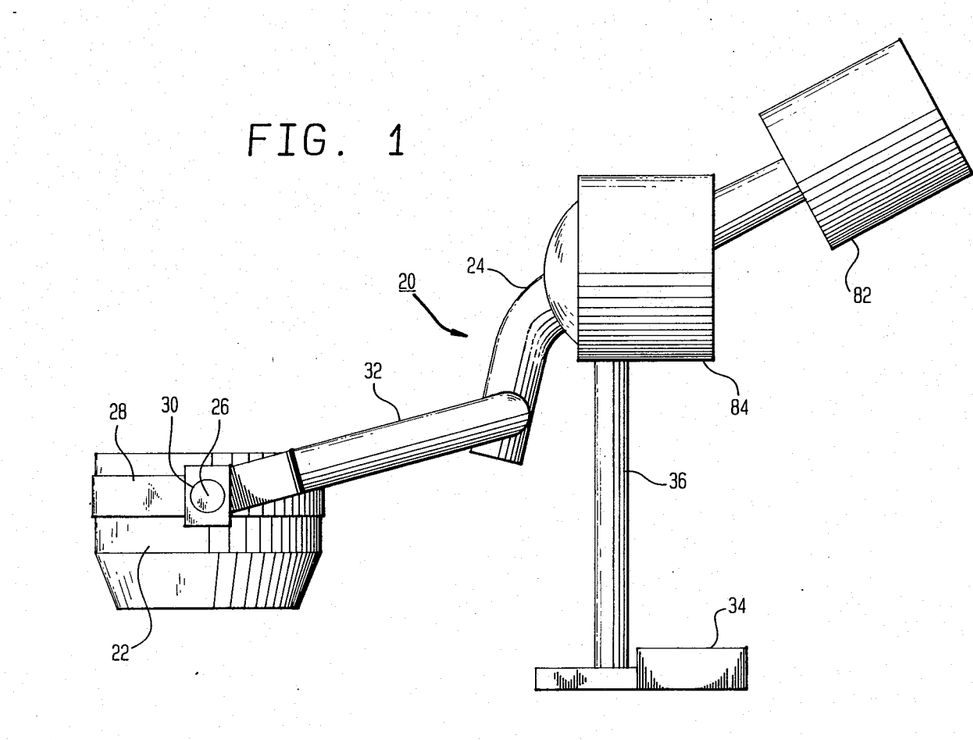
FIG. 1 is a side view of a gamma camera comprising the supporting structure according to this invention.
Figure 2:
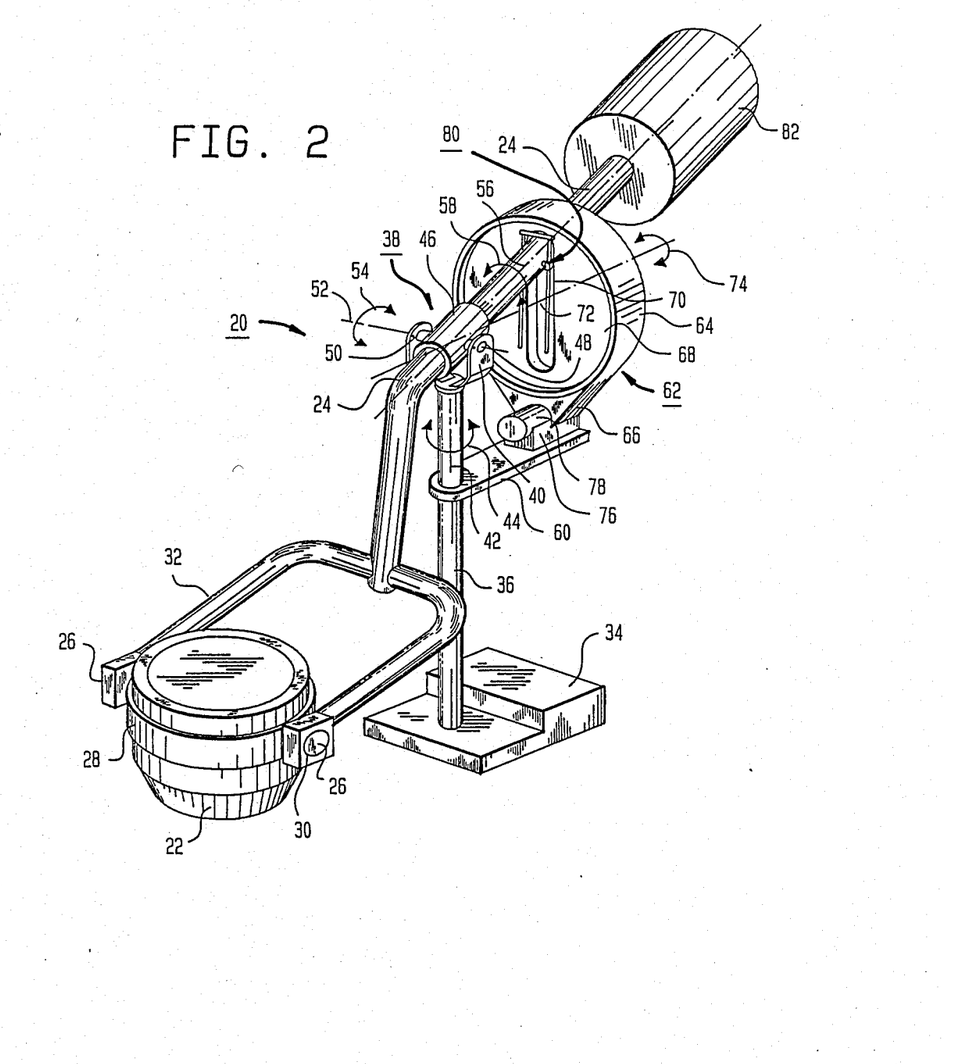
FIG. 2 is an overall perspective view of the gamma camera of FIG. 1 showing the supporting structure according to this invention in more detail.

FIGS. 1 and 2 illustrate an ECT Anger-type scintillation gamma camera 20 comprising a camera head 22 which is pivotably mounted on a bent end of a support arm 24 by means of trunnion 26 of a trunnion ring 28. The trunnion 26 are received in eyes 30 of a yoke portion 32 of the support arm 24.

The support arm 24 is moveably mounted to a base 34 by means of a stanchion 36 and a three axis gimbal 38 on top of the stanchion 36. The gimbal 38 provides for a fulcrum for the support arm 24. It comprises an U-shaped piece 40 which is rotatable on top of the stanchion 36 about vertical axis 42 in the directions of rotational arrow 44. The gimbal 38 further includes a sleeve member 46 mounted in the U-shaped piece 40 by means of trunnions 48, 50 such that it is rotatable about horizontal axis 52 in the directions of rotational arrow 54. The support arm 24 is inserted in the sleeve member 46 so that it is rotatable within the sleeve member about longitudinal arm axis 56 in the directions of rotational arrow 58.

The stanchion 36 further comprises a mounting plate 60 on which a frame 62 is mounted. The frame 62 includes an annular frame portion 64 and a basic frame portion 66. A circular slotted member 68 having a guidance slot 70 is inserted in annular frame portion 64 so that it is rotatable in the annular frame portion 64 about rotational axis 72 in the directions of rotational arrow 74. The basic frame portion 66 includes a mounting support 76 for mounting frame 62 on the mounting plate 60 on the one hand and for mounting a motor drive 78 on top of the mounting support 76 on the other hand. The motor drive 78 is provided for rotating the circular slotted member 68 in the annular frame portion 64 about axis 72. The rotational axis 72 intersects the longitudinal arm axis 56 in the joint provided by the gimbal 38.

According to this invention, the support arm 24 is mounted in the guidance slot 70 of the slotted member 68 in a desired distance from the rotational axis 72 freely slidable along its longitudinal arm axis 56, however non rotatably fixed with respect to the guidance slot 70. A special mounting mechanism for that purpose is indicated in FIG. 2 with the reference numeral 80.

The mounting mechanism 80 of FIG. 2 will later be described in more detail in conjunction with FIGS. 3 and 4.

Another embodiment of such a mounting mechanism will also later be portrayed in connection with FIGS. 7 and 8.

The element 82 in FIGS. 1 and 2 is a counterweight for balancing the weight of the camera head 22. In this embodiment the counterweight 82 is cylindrical. However, any other shape of counterweight 82 symmetrical with respect to rotation about longitudinal arm axis 56 would be suitable for preventing of undesired torques during rotation of the counterweight when rotating the support arm 24 about its longitudinal arm axis 56.

No counterweight is necessary in case that the stanchion is declined with respect to the base such that the structure of declined stanchion and base balance the camera head.

As is also indicated in FIG. 1 all elements 60 and 80 shown in FIG. 2 are enclosed in a housing 84. The input and output windows for the support arm 24 in housing 84 can be covered by slit resilient plastic or rubber folios (not shown in the drawings).

When rotating the circular slotted member 68 in the annular frame portion 64 by means of motor drive 78 the support arm 24 is driven about the joint provided by the gimbal 38 on top of the stanchion 36 so that the camera head 22 traverses an arc with the camera head facing inward and so that a reference line drawn from the fulcrum to the camera head describes a conical surface having the fulcrum in its apex and the arc at its base. The radius of the arc is determined by the distance of the support arm 24, i.e. its longitudinal arm axis 56, from the rotational axis 72 of the circular slotted member 68.

Figure 3:
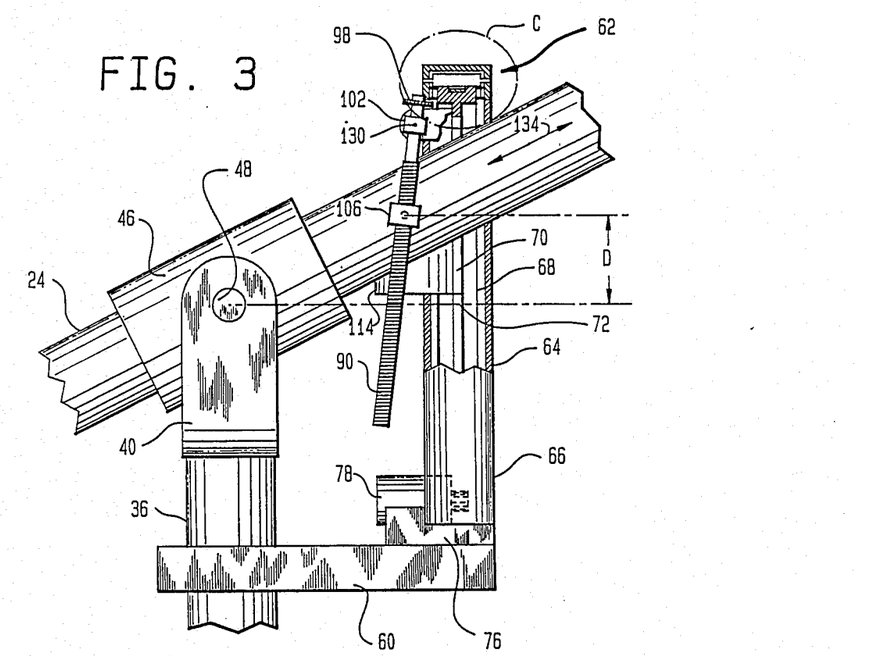
FIG. 3 is a first embodiment of a device for mounting a camera supporting arm in the guidance slot of a rotatable slotted member in a side view.
Figure 4:
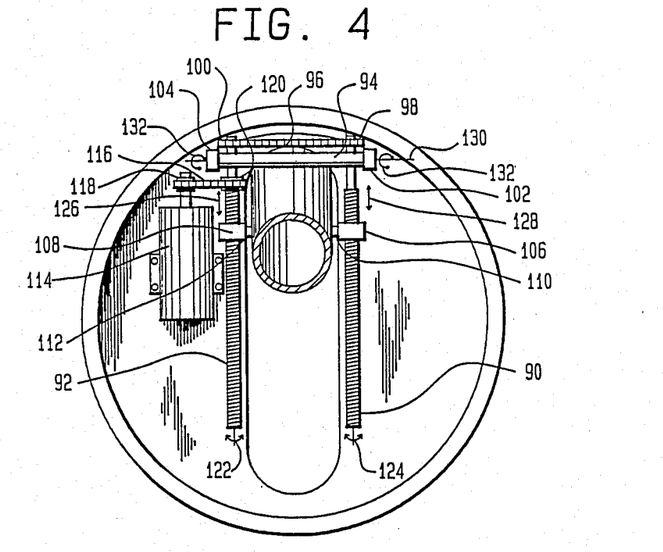
FIG. 4 is the embodiment of FIG. 3 in a front view.

In FIGS. 3 and 4 this distance is generally indicated with D. For providing a desired distance the mounting mechanism 80 for the support arm 24 in the guidance slot 70 of the circular slotted member 68 comprises two acme screws 90, 92 which are connected with each other by means of a tilting bar 94 and a synchronizing chain drive comprising a chain 96 and sprockets 98, 100. The tilting bar 94 is tiltably mounted by means of bearings 102, 104 to the slotted member 68. Nuts 106, 108 which are firmly connected with the support arm 24 by means of turnable pins 110, 112, are slidably mounted on the screws 90, 92, respectively.

When rotating acme screw 92 by means of gear motor 114, which is also mounted on the slotted member 68, via tooth belt 116 (or chain) and sprockets 118 and 120, acme screw 92 is rotated in one or the other of the directions of rotational arrow 122. Synchronously with that also acme screw 90 is rotated in one or the other of the directions of rotational arrow 124.

As a result nuts 106 and 108 move up or down along acme screws 90, 92 in one or the other of the directions of double arrows 126, 128 dependent on the rotational direction of acme screw 92, thereby shifting the support arm 24 in a greater or smaller distance from the rotational axis 72 of slotted member 68.

Since the nuts 106 and 108 are firmly connected with the support arm 24 by means of pins 110 and 112 the mounting mechanism 80 provides for mounting the support arm 24 in the guidance slot 70 of the circular slotted member 68 in a non-rotational fixed position with respect to the guidance slot 70 of the slotted member 68. However, due to the tilting bar 94 both acme screws 90 and 92 are tiltable about bar axis 130 in directions of the tilting arrow 132.

Under these circumstances, the support arm 24 is also mounted by mounting mechanism 80 such that it is freely slidable along its longitudinal arm axis 56 in the directions of double arrow 134. As a result any point on axis 56 has free longitudinal motion with respect to axis 72 as arm 24 is laterally displaced relative to axis 72. Due to that changing distances between the point of attachment of the support arm 24 to the circular slotted member 68 and the universal joint of the gimbal 38 according to changing tilt angles can now very easily be compensated in a technically very simple manner. Compared with U.S. Pat. No. 4,417,143, a complicated telescoping coupling member is no longer necessary.

Figure 5:
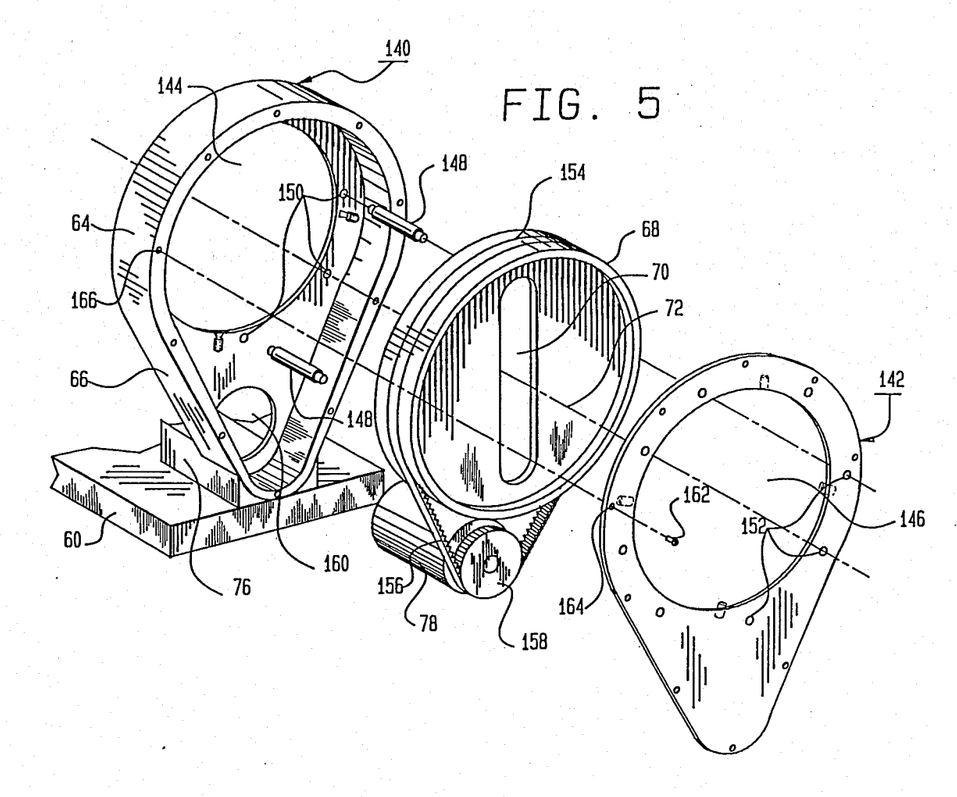
FIG. 5 is an exploded view of a device for rotating the slotted member.
Figure 6:
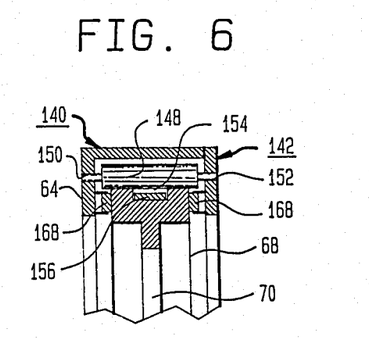
FIG. 6 is a partial cross section of the rotating device with inserted rotatable slotted member.

FIG. 5 illustrates an exploded view of the drive mechanism for the circular slotted member 68. FIG. 6 shows an enlargement of partial cross section C in FIG. 3, i.e. a partial cross section of the drive mechanism of FIG. 5 in case all members are combined together.

As can be seen from FIGS. 5 and 6, the annular frame portion 64 comprises a frame body 140 and a body cover 142 having each a circular window 144 and 146, respectively. Horizontal rollers 148 can be inserted with one end in bores 150 of the frame body 140. The other ends of the rollers 148 are designated for being inserted in corresponding bores 152 in the body cover 142 when mounting the body cover 142 on the frame body 140 after having inserted the slotted member 68 and its motor drive 76 in the frame body 140.

The circular slotted member 68, having a T-shaped cross section comprises a circular groove 154 along its circumference. The groove 154 comprises teeth which fit to the teeth of a tooth belt 156 which is driven by motor drive 78 via sprocket 158. A chain can also be utilized instead of a tooth belt.

The frame body 140 also comprises a circular opening 160 for extending of motor drive 78 through the frame body 140 to the outside mounting support 76. The body cover ring 142 can be mounted on frame body 140 by screws 162 via screw holes 164 and 166.

The elements 168 in frame body 140 are side rollers which keep the circular slotted member 68 in a central upright position on horizontal rollers 148 in the interior of the annular frame portion 64 of the frame 62. The complete system preferably comprises four pairs of side rollers 168, which are mounted in 90° steps along the circumferences of the annular portions of frame body 140 and body cover ring 142 as indicated in FIG. 5.

Figure 7:
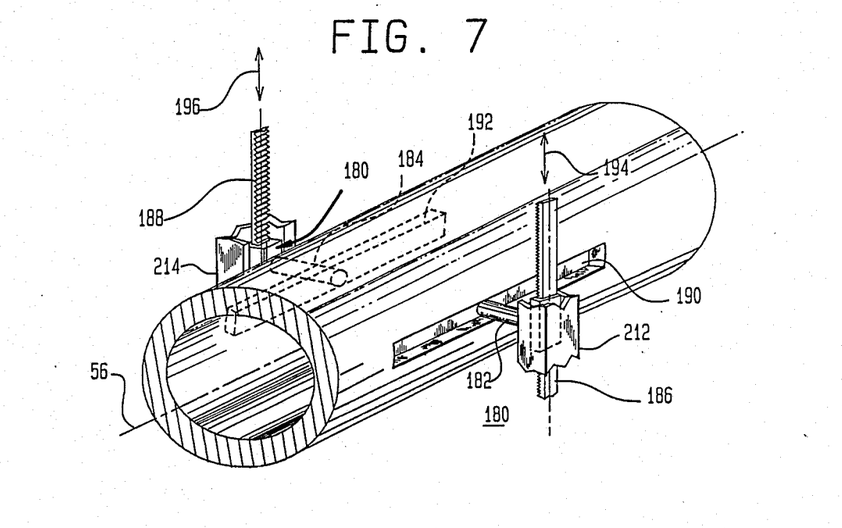
FIG. 7 is a second embodiment of a device for mounting a camera supporting arm in the guidance slot of a rotatable slotted member.
Figure 8:
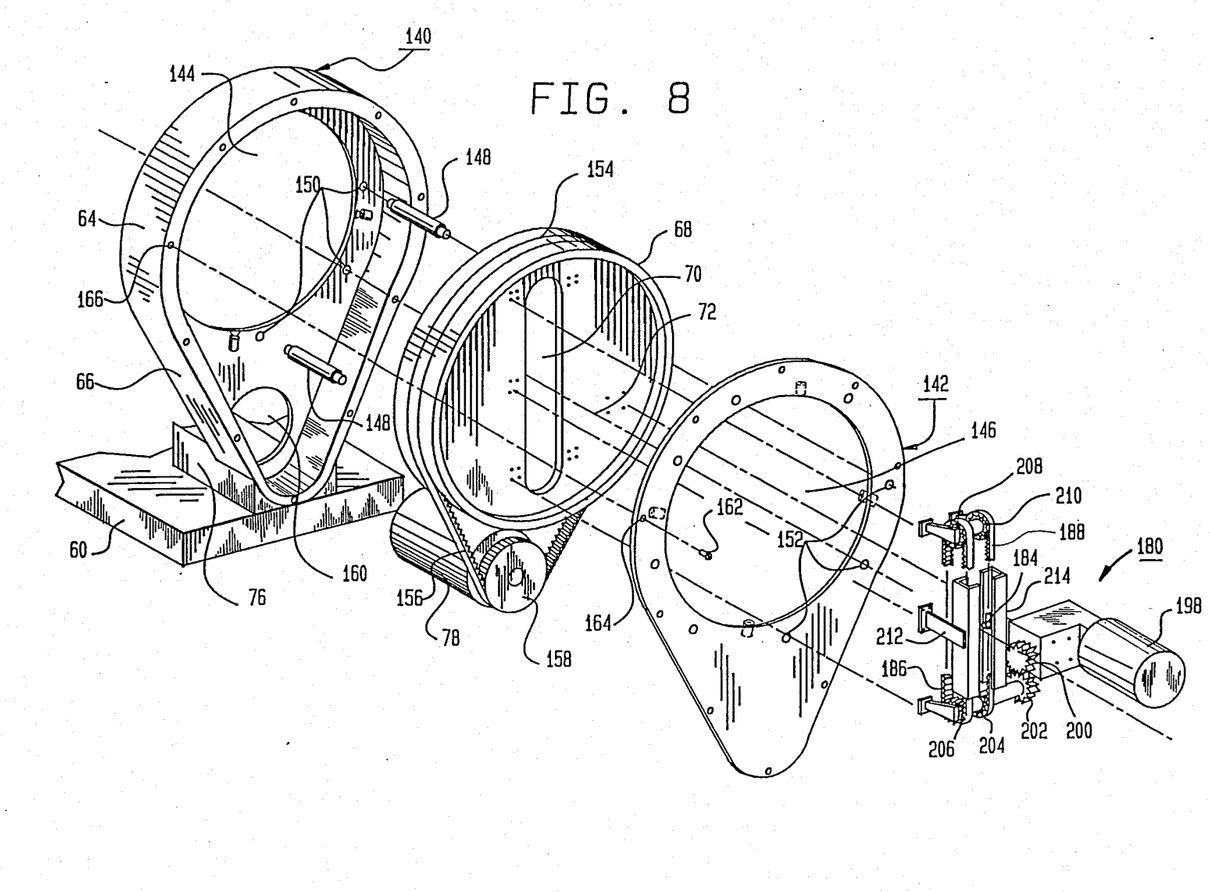
FIG. 8 is an exploded view of a device for rotating the slotted member in conjunction with the second embodiment of FIG. 7.

FIGS. 7 and 8 illustrate another embodiment of a mounting mechanism for mounting the support arm 24 in the guidance slot 70 of the slotted member 68 such that the arm 24 is freely slidable along its longitudinal arm axis 56, however non-rotatably fixed with respect to the guidance slot 70. This mounting mechanism, which is generally designated with 180 in FIG. 7 and 8, comprises a first and second pins 182, 184 each being mounted on a first and second tooth belts 186, 188 (or chains), respectively. The first pin 182 intrudes into a first longitudinal slot 190 and the second pin 184 intrudes into a second longitudinal slot 192 of the support arm 24. By synchronously moving the first and second tooth belts 186, 188 (or chains) up or down in the direction of double arrows 194, 196 the tilting angle of the support arm can be changed. At the same time, when changing the tilting angle the support arm 24 is allowed to slide along its longitudinal arm axis 56 by means of slots 190, 192 on pins 182 and 184. Again the distance between universal joint (gimbal 38) and point of attachment (pins 182, 184) of the support arm to slotted member 68 is automatically compensated in a technically very simple manner.

As indicated in FIG. 8 the first and second tooth belts 186, 188 (or chains) are driven by a motor 198 via sprockets 200, 202, 204, 206, 208 and 210. Rails 212, 214 are provided for better guidance of the pins 182, 184 moved by the belts 186, 188. The complete mounting mechanism 180 together with the driving system 186, 188, 198 to 214 is again mounted on the circular slotted member 68 and rotates together with the latter one.

Having thus described the invention with particular reference to the preferred forms thereof, it will be obvious to those skilled in the art to which the invention pertains, after understanding the invention, that various changes and modifications may be made therein without departing from the spirit and scope of the invention as defined by the claims apended hereto. For example, instead of mounting mechanisms 80 and 180 other mechanism, such as for example a piston-cylinder mechanism utilizing clamping against lateral arm displacement, may be used.

What is claimed is:

1. Structure for supporting a detector head, comprising
   (a) an arm having a distal end supporting the head and having a longitudinal arm axis;
   (b) a base;
   (c) a joint mounted on the base and moveably supporting the arm;
   (d) a slotted member rotatably mounted to the base at a predetermined distance from the joint, said slotted member including means for mounting the arm in the guidance slot at a predetermined distance from the rotational axis in a manner that the arm is freely slidable along its longitudinal arm axis, and is non-rotatably fixed with respect to the guidance slot; and
   (e) means connected between base and slotted member for rotating the slotted member about its rotational axis.

2. The structure according to claim 1, wherein the slotted member is rotatably mounted at the base with its rotational axis intersecting the longitudinal arm axis in the joint.

3. The structure according to claim 1, wherein the means for mounting the arm in the guidance slot comprises
   (a) a screw having a first end which is rotatably attached to the slotted member in a pivot point and having a second free end;
   (b) a nut held in threaded engagement with the screw and being unrotatably connected with the arm; and
   (c) a means for rotating the screw;
wherein, when rotating the screw, the nut moves along the screw thereby on the one hand moving the arm into the predetermined distance from the rotational axis of the slotted member and on the other hand turning the screw about the pivot point on the slotted member, so that the arm is freely slidable along its longitudinal arm axis.

4. The structure according to claim 1, comprising
   (a) a first screw on one side of the arm, said first screw having a first end and a free second end;
   (b) a second screw on the other diametrically opposite side of the arm, said second screw having a first end and a free second end;
   (c) a first nut held in threaded engagement with the first screw and being nonrotatably connected with the arm on the side of the first screw;
   (d) a second nut held in threaded engagement with the second screw and being nonrotatably connected with the arm on the side of the second screw; and
   (e) means for rotatably connecting the first and second screws with each first screw end with the slotted member.

5. The structure according to claim 3, further comprising
   (a) a tilting bar for connecting the first ends of the first and second screw with each other; and
   (b) means for rotatably connecting the tilting bar with the slotted member.

6. The structure according to claim 3, wherein the means for rotating the screw comprises a transmission for driving the screw and a motor for driving the transmission.

7. The structure according to claim 1, wherein the means for mounting the arm in the guidance slot comprises
   (a) a pin;
   (b) a slot in the arm which extends along the longitudinal arm axis, said pin being inserted in the slot so that the arm is freely slidable along its slot on the pin, however non-rotatably fixed by the pin in the slot; and
   (c) means connected with and for moving the pin relatively to the slot, so that the arm moves into the predetermined distance from the rotational axis of the slotted member.

8. The structure according to claim 7, comprising
   (a) a first and second slots extending along the longitudinal arm axis on diametrically opposite sides of the arm;
   (b) a first pin inserted in the first slot and a second pin inserted in the second slot; and
   (c) means connected with and for synchronously moving the first and second pins relatively to the first and second slots, so that the arm moves into the desired distance from the rotational axis of the slotted member.

9. The structure according to claim 7, wherein the means connected with and for moving the pin comprises a transmission connected with the pin and a motor for driving the transmission.

10. The structure according to claim 1, wherein the means for rotating the slotted member comprises a transmission connected with the slotted member and a motor for driving the transmission.

11. The structure according to claim 1, wherein a circular slotted member is rotatably mounted in an annular frame portion of a frame mounted on the base.

12. The structure according to claim 11, wherein the base comprises a stanchion and the arm is moveably mounted in a joint on top of a stanchion, and wherein the frame is mounted on a mounting plate which is connected with the stanchion.

13. The structure according to claim 1, further comprising a counterweight wherein the detector head is mounted at a first end of the arm and the counterweight is mounted at an opposite second end of the arm and wherein the counterweight has a shape symmetrical with respect to rotation about the longitudinal arm axis.

14. The structure according to claim 1, wherein the joint is a gimbal.

* * * * *